(12) United States Patent
Decke et al.

(10) Patent No.: US 7,602,189 B2
(45) Date of Patent: Oct. 13, 2009

(54) MAGNETIC RESONANCE EXAMINATION PLATFORM WITH INDEPENDENTLY MOVEABLE BED AND ANTENNA DEVICE

(75) Inventors: Guenther Decke, Hemhofen (DE); Hubertus Fischer, Bamberg (DE); Wilfried Schnell, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 12/166,725

(22) Filed: Jul. 2, 2008

(65) Prior Publication Data

US 2009/0027053 A1 Jan. 29, 2009

(30) Foreign Application Priority Data

Jul. 2, 2007 (DE) ........................ 10 2007 030 568

(51) Int. Cl.
*G01V 3/00* (2006.01)
(52) U.S. Cl. ........................ 324/318; 324/309
(58) Field of Classification Search ......... 324/300–322; 600/407–445
See application file for complete search history.

(56) References Cited

U.S. PATENT DOCUMENTS

| 5,808,468 | A | 9/1998 | Bis et al. |
| 6,160,400 | A | 12/2000 | Friedrich et al. |
| 6,529,764 | B1 | 3/2003 | Kato et al. |
| 6,927,573 | B2 * | 8/2005 | Eberler et al. ................ 324/309 |
| 7,266,406 | B2 * | 9/2007 | Kroeckel ..................... 600/410 |
| 7,446,531 | B2 * | 11/2008 | Schnell et al. .............. 324/318 |
| 7,490,377 | B2 * | 2/2009 | Ahlman ..................... 5/81.1 R |
| 2002/1380001 | | 9/2002 | Kroeckel |
| 2005/0174117 | A1 | 8/2005 | Greim et al. |
| 2007/0035301 | A1 | 2/2007 | Nakabayashi et al. |
| 2009/0083907 | A1 * | 4/2009 | Ahlman ........................ 5/620 |

FOREIGN PATENT DOCUMENTS

JP 08257013 A 10/1996
WO WO 2006/131863 12/2006

* cited by examiner

*Primary Examiner*—Brij B Shrivastav
(74) *Attorney, Agent, or Firm*—Schiff Hardin LLP

(57) ABSTRACT

An examination platform for a magnetic resonance apparatus has a patient bed for supporting a patient, a local antenna device for acquisition of magnetic resonance signals, and a drive device arranged at the patient bed. The drive device is coupled with the local antenna device. The local antenna device thus can be moved parallel to the longitudinal axis of the patient bed independently of a movement of the patient bed. A magnetic resonance apparatus and a method for acquisition of image data of a patient employ such an examination platform.

18 Claims, 8 Drawing Sheets

S - S'

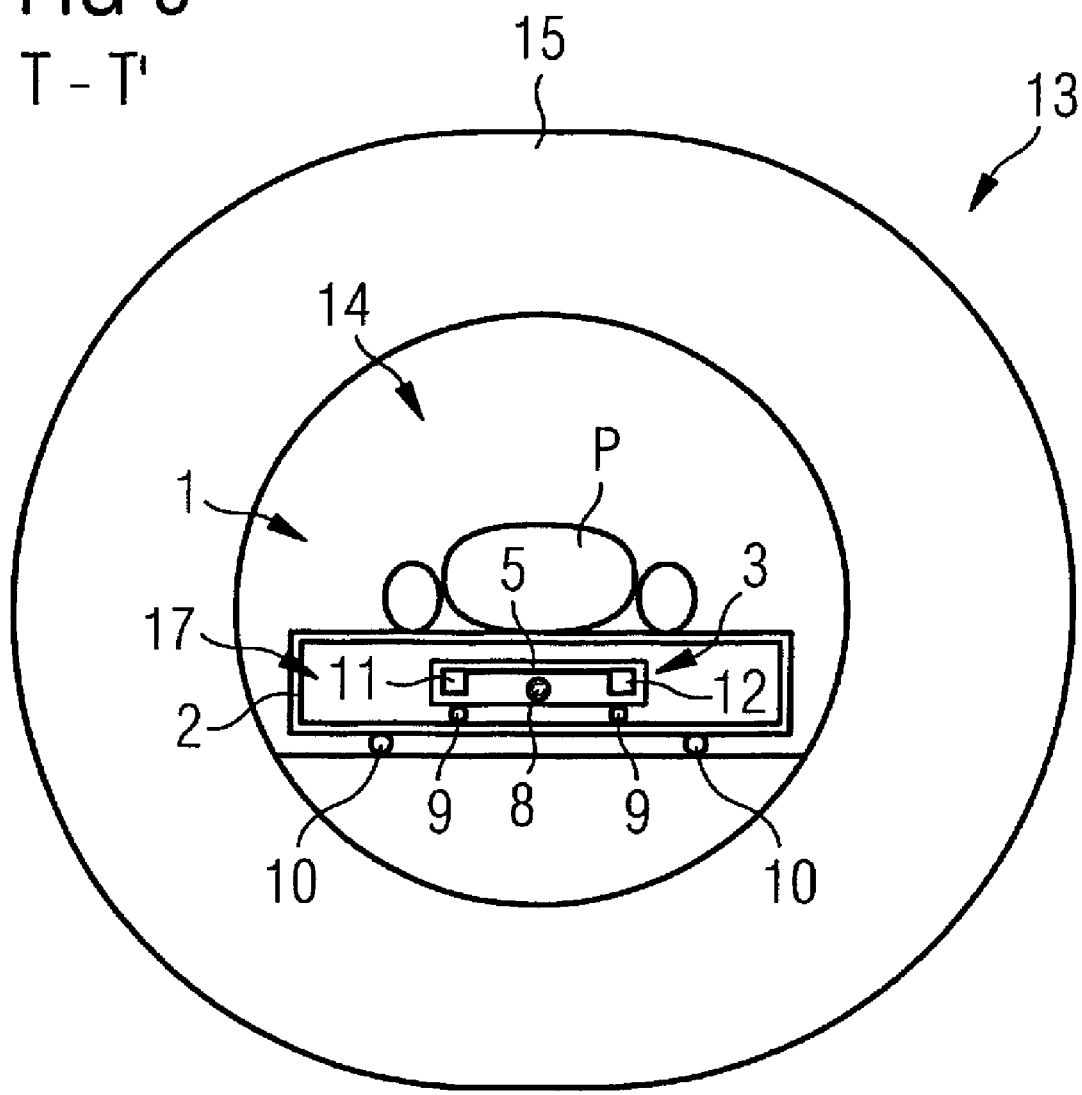

MAGNETIC RESONANCE EXAMINATION PLATFORM WITH INDEPENDENTLY MOVEABLE BED AND ANTENNA DEVICE

BACKGROUND OF THE INVENTION

1. Field of the Invention

The present invention concerns an examination platform for a magnetic resonance apparatus with a movable patient bed, a movable local antenna device for acquisition of magnetic resonance signals, and a drive for moving the bed. The invention also concerns a magnetic resonance apparatus with such an examination platform as well as a method for acquisition of image data of a patient with a magnetic resonance apparatus.

2. Description of the Prior Art

Medical technology imaging systems today assume an important role in the examination of patients. The depictions generated by the imaging systems of the internal organs and structures of the patients are used for diagnosis of pathological causes, for planning of operations, in the implementation of operations, as well as for preparation of therapeutic measures. Examples of such imaging systems are computed tomography systems, ultrasound systems, angiography devices, positron emission tomography systems and magnetic resonance systems.

With a magnetic resonance examination of specific organs or body parts of a patient, surface antennas are increasingly used for acquisition of the magnetic resonance (MR). In the examination these surface antennas are arranged relatively close to the body surface, optimally directly on the organ or body part of the patient to be examined. The surface antennas are frequently executed as a coil and are often designated as "local coils" in the technical literature due to the limited spatial examination region. In contrast to larger antennas arranged further from the patient that normally are used to generate an entire slice image through a patient, the surface antennas have the advantage that they are arranged closer to the regions of interest. The noise component caused by the electrical losses within the body of the patient is thereby reduced, which results in the signal-noise ratio of a surface antenna being in principle better than that of a more remote antenna. A disadvantage is that a single surface antenna is only able to generate an effective image within a specific spatial extent which lies on the order of the diameter of the conductor loops of the surface antenna. The usage possibilities for such individual surface antennas are therefore very limited due to the limited observation range (field of view). The observation range can in fact be expanded by enlarging the diameter of the conductor loop of the surface antenna. However, an increase of the electrical losses in the body of the patient and an associated increase in noise result from the enlargement of the conductor loop. In the use of a single surface antenna, a compromise must always be selected between an optimally good resolution and an optimally large observation range.

One possibility to enlarge the observation range without reducing the resolution to the same degree is to use multiple individual surface antennas arranged adjacent to one another, i.e. to use an entire field of antenna elements (for example an antenna array), that together form one large surface antenna. However, one problem with the use of multiple antenna elements is that the patient can perceive the coverage of body regions over a large area as objectionable, which in extreme cases sometimes leads to a termination of the examination. Moreover, the application of additional sensors (such as electrocardiogram electrodes) is made more difficult given a coverage of the patient over a large area. The high costs that arise due to the purchase of numerous antenna elements represents an additional disadvantage. Moreover, the handling of the individual antenna elements of the multiple elements (i.e. the application and removal of the antenna elements) is time-consuming and therefore cost-intensive. Moreover, the probability of an incorrect placement of the antenna elements on the body of the patient increases with the number of antenna elements, which can lead to an impairment of the image quality. A further disadvantage of the surface antennas placed on or below a patient is in that the position of the surface antennas relative to the body of the patient can no longer be varied during an examination. This means that, given a less suitable placement of the surface antennas, either a poorer image quality must be accepted or a termination of the image acquisition with subsequent, more correct placement is necessary.

Methods and devices to avoid the disadvantages of surface antennas arranged directly on the body of the patient are already known. For example, in United States Patent Application Publication 2002/0138001 a magnetic resonance apparatus is described which itself has a surface antenna that can be lowered from above onto a recumbent patent by a corresponding device. However, the application of a surface coil in the examination space of the magnetic resonance apparatus reduces the space available for the patient. In particular, examinations are known as "head first" examinations in which the patient is inserted head first into the magnetic resonance apparatus can lead to claustrophobic reactions in the patient due to the reduced space. Moreover, the described stationary arrangement at the magnetic resonance apparatus means that the position of the surface coil relative to the electromagnetic fields emitted by the magnetic resonance apparatus cannot be altered. An optimization of the acquisition properties of the surface antenna due to a movement relative to these fields is therefore not possible.

The same is true for the design in United States Patent Application Publication 2005/0174117. There a local coil with flexible properties is described but without information as to how a larger range of the patient can be efficiently examined.

Furthermore, a device in which a local coil is integrated into a bed is described in WO 2006/131863 A1. It is disadvantageous that the local coil therein assumes a stationary spatial position after the insertion of the patient. This means that the position of the local coil can then no longer be optimized, for example in order to correct disadvantageous couplings with other coils in the magnetic resonance apparatus. Moreover, the document refers to coils integrated into a bed, such that essentially only regions on the back side of the patient (such as the spinal column) can be examined.

SUMMARY OF THE INVENTION

An object of the present invention is to provide an improved alternative relative to this known prior art.

The above object is achieved in accordance with the present invention by an examination platform for a magnetic resonance apparatus, including a patient bed that is movable along a longitudinal axis thereof for supporting a patient relative to a magnetic resonance data acquisition unit (scanner), a local antenna device for acquisition of magnetic resonance signals, said local antenna device being mounted so as to be moveable parallel to the longitudinal axis of the patient bed independently of movement of the patient bed, and a drive device mounted at the patient bed and coupled with the local antenna for effecting the aforementioned movement of the local antenna device parallel to the longitudinal axis of the patient bed.

A basis of the examination platform to the invention is to specify local antenna devices that can be moved independently of movement of a patient bed on which the patient is supported, this movement ensuing parallel to the longitudinal axis of the patient bed and being effected by a drive device. The local antenna device includes one or more surface antennas or local coils for acquisition of magnetic resonance signals which serve for the generation of the patient image data. In many cases the patients are people, but the use of the term "patient" does not preclude the use of the inventive devices, apparatuses and methods in the examination of animals.

Moreover, usage in the examination of healthy people is included, for example for prophylaxis or in the examination of test subjects in a clinical study.

Relative to the typical surface antennas placed on or below the patient, the examination platform according to the invention has the advantage that, due to the mobility of the local antenna device, only a few antennas (possibly even only a single antenna) are necessary to be able to acquire a wide body region of the patient in the image generation. The cost-intensive procurement and time-consuming application of many surface antennas is therefore provided. Moreover, with examination platform according to the invention the local antenna device can be moved relatively simply and flexibly after the positioning of the patient. Possible incorrect positionings of the surface antennas can be corrected by moving the local antenna device without the patient having to be moved out from the magnetic resonance apparatus for this purpose. The same applies for the position of the antennas relative to the magnetic fields and electromagnetic fields radiated by the magnetic resonance apparatus. Here an optimal relative position is also dependent on the individual properties of the patient, for example the patient's physique. The examination platform according to the invention allows an optimization of the relative position since the local antenna device can be moved independently to the greatest possible extent both relative to the patient and relative to the magnetic resonance apparatus, i.e. specifically relative to the magnets and antennas contained in the magnetic resonance apparatus. Furthermore, with the examination platform according to the invention it is no longer necessary for the antennas to be already positioned on the patient before the insertion of the patient into the magnetic resonance apparatus. Negative perceptions by the patient (for example anxieties or claustrophobia) should therefore occur to a significantly lesser degree with the examination platform according to the invention.

A method according to the invention for acquisition with a magnetic resonance apparatus of image data of a patient on a movable patient bed includes moving a local antenna device with a drive device coupled to the local antenna device, the movement of the local antenna device ensuing independently of movement of the patient bed and parallel to the longitudinal axis of the patient bed. The disadvantages of the prior art cited in the preceding can be avoided with the method according to the invention.

In an embodiment of the examination platform according to the invention, the local antenna device is arranged essentially above the patient bed. The patient is therefore located at least partially between the patient bed and the local antenna device. Given a movement of the local antenna device relative to the patient bed, the local antenna device thus moves essentially across the patient and, depending on the embodiment of the local antenna device, also laterally past the patient. Both movement directions (i.e. in the direction of the patient head and in the direction of the patient feet) are thereby possible.

The local antenna device mounted above the patient bed is preferably fashioned with a bridge-like shape in a plane perpendicular to the longitudinal axis of the patient bed, and in particular follows the shape of a circular arc.

The housing of the local antenna device mounted above the patient bed preferably is formed of non-magnetic plastic in order to ensure an optimally small influencing of the electromagnetic fields by the housing. Such plastics are typically reinforced with glass fiber components and are commercially available under the designation DURETHAN® BKV30 by Lanxess AG. The antennas or local coils contained in the local antenna device are formed of an electrically conductive material such as copper which is applied on a base material in the form of conductor traces. Materials as they are known for circuit board manufacture are used as base materials. For example, FR-4 (flame retardant 4) or the materials sold by Rogers are examples.

In a preferred embodiment of the invention, the local antenna device is fashioned at least partially with flexible materials and has a bending device with which the distance between the patient and the part of the local antenna device fashioned with the flexible materials can be adjusted. With such a local antenna device, the shape of the local antenna device can be adjusted depending on the position of the local antenna device along the longitudinal axis of the patient bed, so that the distance from the patient is made to be as minimal as possible in order to ensure a good acquisition of the magnetic resonance signals by the antennas or local coils. This means that signals can be acquired with relatively low noise portion in all positions of the local antenna device, even in examinations that acquire a wide region of the patient body (for example from the lower legs to the chest), since the shape of the local antenna device can be adapted to the respective anatomical properties of the patient.

In a further particularly preferred embodiment of the examination platform according to the invention, the local antenna device has a first local antenna device element and a second local antenna device element, wherein the first and/or the second local antenna device element being fashioned and/or arranged such that it can be moved in a plane perpendicular to the longitudinal axis of the patient bed. In such an embodiment it is also possible without flexible components of the local antenna device, to adjust the distance between the patient and the antennas contained in the local antenna device elements by a movement of the local antenna device elements. This can ensue with the goal of keeping the distance as minimal as possible so that the noise component of the antenna signal remains sufficiently small. Furthermore, such an embodiment of the local antenna device also permits the local antenna device elements to be positioned near the patient body only for the moment of the image acquisition and at all other times to be at a large distance from the patient, so the aforementioned anxiety or claustrophobia reactions by the patient should be reduced. Embodiments are also possible that use more than two local antenna device elements, so an even better capability of adaptation to the shape of the patient bed can result.

In a preferred embodiment the local antenna device elements are each designed to include at least one individual antenna for acquisition of magnetic resonance signals. Alternatively, the local antenna device elements can be designed such that these each includes only a partial antenna, and a combined antenna for acquisition of the magnetic resonance signals arises only by interaction of multiple local antenna device elements. The combined (overall) antenna is preferably fashioned by capacitive and/or inductive and/or galvanic coupling between the partial antennas respectively contained in the local antenna device elements.

In a further preferred embodiment of examination platform according to the invention, the local antenna device is integrated at least partially into the patient bed. The patient bed exhibits a void within which the part of the local antenna device integrated into the patient bed can be moved. The part of the local antenna device integrated into the patient bed is not visible by the patient, and therefore a movement of the local antenna device along the patient is barely perceived as objectionable. This is particular the case when the drive device is entirely integrated into the patient bed in addition to the local antenna device. Such, an examination platform according to the invention then does not externally differ from a conventional patient bed without movable local coils or antennas. Moreover, especially if the top side of the patient bed is relatively thin, an advantageous (i.e. large) signal-noise ratio can be achieved with the integration of the local antenna device into the patient bed since the antennas can be moved relatively close to the patient.

Especially with the local antenna device integrated into the patient bed, but also with the local antenna device arranged above the patient bed, in an embodiment the local antenna device can additionally be moved in a direction that differs from a direction parallel to the longitudinal axis of the patient bed. For example, a local antenna device integrated into the patient bed can be moved perpendicularly to the longitudinal axis of the patient bed and within a plane parallel to the bed plane of the patient bed. Then it is possible to position the local antenna device such that boundary regions of the patient body can also be rendered well in the image generation.

In a preferred embodiment of the examination platform, the local antenna device is integrated into a unit with a number of preamplifiers and/or a number of detuning devices. This means that, given a movement of the local antenna device, the preamplifiers and/or detuning devices experience a movement corresponding to the movement of the local antenna device. The preamplifiers thereby amplify the magnetic resonance signals acquired by the antennas of the local antenna device. In a preferred embodiment, the preamplifiers are coupled with an antenna via an adaptive network. Due to the mutual movement of the preamplifiers with the antennas of the local antenna device, connection lines can be made relatively short between the antennas and the preamplifiers, so disruptive influences that are caused or introduced by the connection lines can be reduced. Furthermore, in an embodiment the preamplifiers can be switchable. This is advantageous if antennas with preamps are connected via a switching device with a common acquisition device, with the switching device connecting only some of the preamplifiers with the acquisition device at a time. The switchable preamplifiers that are at least temporarily not connected with the acquisition device can be disconnected in an advantageous manner.

The acquisition properties of the antennas contained in the local antenna device can be adjusted with the detuning devices. Suitable detuning devices are known in the prior art. There they serve to, among other things, adjust the resonance circuit formed by the antenna so that this is active only in the time intervals relative for the image acquisition. Moreover, in the examination platform according to the invention, detuning devices are advantageously to be used to compensate disadvantageous inductive couplings with other antennas or coils contained in the magnetic resonance apparatus via an adaptation of the acquisition properties of the antennas of the local antenna device. Moreover, the integration of the detuning device is particularly advantageous when the local antenna device includes multiple local antenna device elements since these can have decouplers between the contained antennas or partial antennas, these decouplers being distinguished from one another by a dependency on their relative position. A detuning device can reduce or compensate disadvantageous couplings in an advantageous manner dependent on the position of the local antenna device elements.

The drive device of a bed device according to the invention can be electromotive, i.e. it can be formed by one or more electromotors, for example. Both linear and rotation drives can thereby be used. Additional embodiments of the drive device contain hydraulic or pneumatic variants that are particularly advantageous when the drive device is located near the magnetic field of the magnetic resonance apparatus since, with a suitable construction, these variants are not impaired by a magnetic field or a radio-frequency field, and also do not influence these fields themselves.

In addition to a direct connection of the drive device with the local antenna device, in a bed device according to the invention a coupling of the drive device with the local antenna device can also ensue via jacketed cables (Bowden controls) and/or shafts and/or chains and/or toothed racks and/or cogwheels and/or hydraulic telescopic cylinders and/or pneumatic telescopic cylinders. Couplings that use non-magnetic and non-conductive materials, for example shafts made from non-magnetic, non-conductive plastic, are particularly preferred.

In a preferred embodiment of the examination platform, the local antenna device is connected via a number of rail elements with the patient bed, and the rail elements are arranged essentially parallel to the longitudinal axis of the patient bed. In a further embodiment the local antenna device is connected via a number of rollers with the patient bed, with a roller device rotating the rollers essentially parallel to the longitudinal axis of the patient bed. Moreover, an embodiment is possible in which the local antenna device is elevated and/or moved by exhausting air or other gaseous substances relative to the patient bed. Further embodiments for movement of the local antenna device include raising and/or lowering the local antenna device relative to the patient bed, with the raising and/or lowering (among other things) being effected by a magnetic field. It is possible for a magnetic field that is already generated by the magnetic resonance apparatus to be applied for such a movement.

The examination platform according to the invention can be integrated in an advantageous manner into a magnetic resonance apparatus, so the patient can be positioned within the acquisition space with the examination platform, at least along the longitudinal axis of the patient bed. The region of a magnetic resonance apparatus that is usable for the image generation is designated as an acquisition space. This region can be shorter along the longitudinal axis of the patient bed than a patient, such that the patient must be moved relative to the acquisition space for the imaging of larger body regions. According to the prior art this movement is usually implemented by a movement of the patient bed along its longitudinal axis. With an examination platform according to the invention, it is now possible in an advantageous manner to move the local antenna device independently of the movement of the patient bed. The antennas or local coils contained in the local antenna device thus can be positioned so as to be located at a predetermined position during the acquisition of image data, independent of the position of the patient bed. The positioning can be selected such that the predetermined position lies in the center of the acquisition region in which (usually) a particularly homogeneous magnetic field and radio-frequency field exist for excitation of the nuclear spins.

In addition to an integration of the examination platform into a magnetic resonance apparatus, embodiments of the invention are conceivable in which the magnetic resonance apparatus has an interface for coupling with the examination platform according to the invention, so that with the examination platform, the patient can be positioned within the acquisition space of the magnetic resonance apparatus, at least along the longitudinal axis of the patient bed.

The examination platform or the magnetic resonance apparatus preferably has a regulation or control device that is configured to regulate or control the movement of the local antenna device dependent on a movement of the patient bed such that the local antenna device is always located at the same position in the acquisition space during an acquisition of image data, independent of the position of the patient bed.

In a preferred embodiment of the method according to the invention the local antenna device is moved such that the local antenna device is always located at the same position in the acquisition space during an acquisition of image data, independent of the position of the patient bed. It is possible for the local antenna device to be moved relative to the patient bed before and/or after a movement of the patient bed in order to compensate for the movement of the patient bed. The local antenna device also can be moved simultaneously with a movement of the patient bed. This is particularly advantageous if an examination known as a "move during scan" examination is conducted in which the patient bed (and therefore the patient) moves during the image acquisition. The simultaneous movement of the local antenna device then ensures that the local antenna device is located at a predetermined position in the acquisition space in spite of the movement of the patient bed.

Alternatively, the local antenna device can be moved such that the distance to antennas or local coils that move with the patient bed assume only predetermined values during the acquisition of the image data. Such a "discretization" or "quantization" of the distances between the local antenna device and an antenna or local coil affixed to the bed or patient is particularly advantageous when couplings can occur between both coils that assume advantageous values for the imaging at specific spacings, or when an optimally constant coupling is sought.

In one embodiment of the inventive method, the local antenna device or local antenna device elements are moved in a plane perpendicular to the longitudinal axis of the patient bed before and/or during the acquisition of the image data such that the local antenna device or the local antenna device elements converge in the plane. This has the advantage that the signal-noise ratio of the acquired magnetic resonance signals increases due to the reduced distance.

In a preferred embodiment of the method according to the invention, the local antenna device is positioned in the acquisition space of the magnetic resonance apparatus before the acquisition of the image data by movement of the patient bed in the direction of the head of the patient, and the local antenna device is moved in the direction of the head of the patient during and/or after the movement of the patient bed. The situation is therefore advantageously avoided (especially given use of local antenna devices that are at least partially located above the patient) of the local antenna device having to pass the head region of the patient upon insertion of the patient into the acquisition region.

BRIEF DESCRIPTION OF THE DRAWINGS

FIG. 9 is a schematic cross-section illustration through the magnetic resonance apparatus according to FIG. 8 in the section plane T-T'.

DESCRIPTION OF THE PREFERRED EMBODIMENTS

Figure 1:
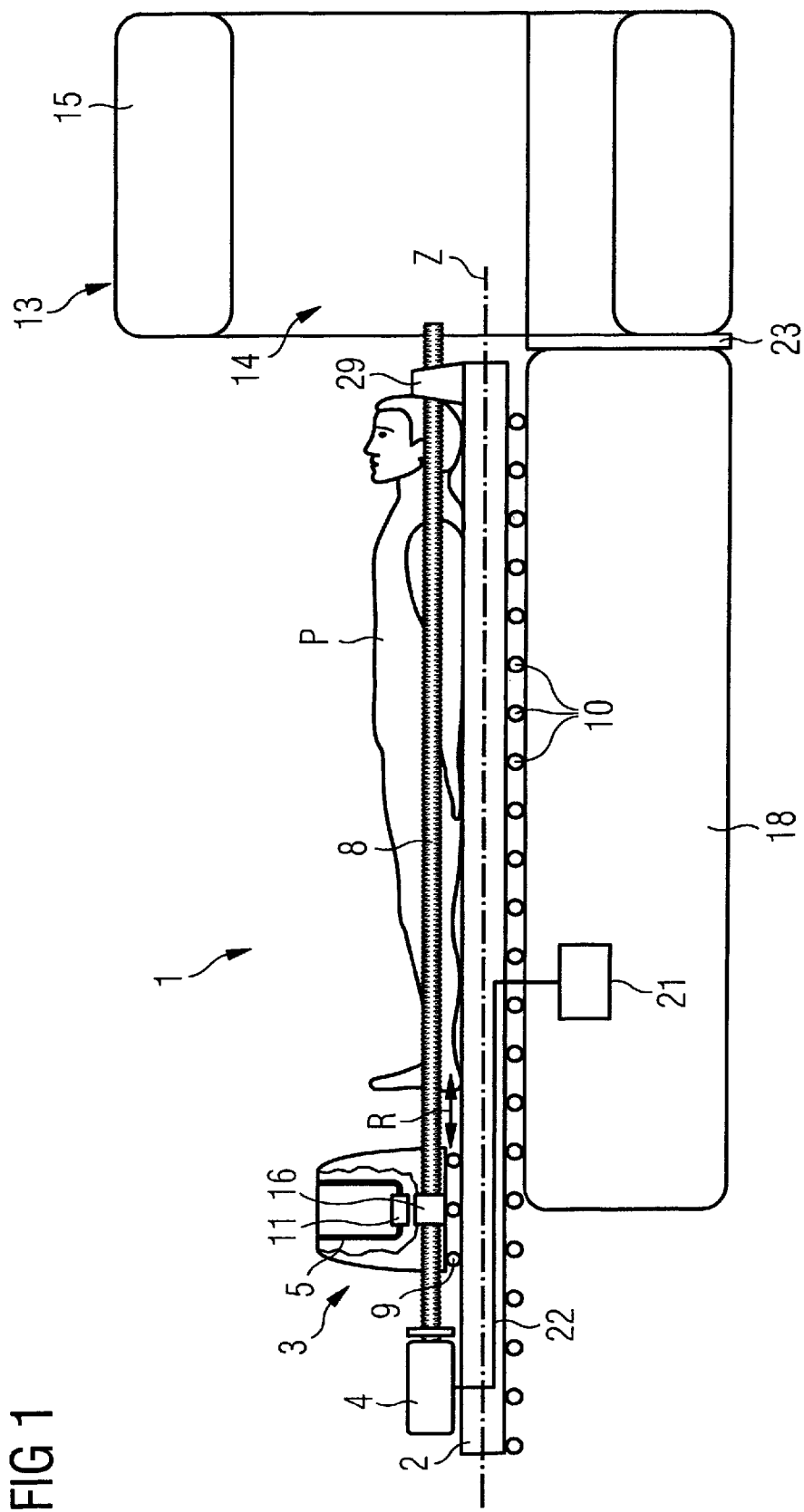
FIG. 1 schematically shows a side view of an examination platform according to the invention with a local antenna device arranged above a patient bed, as well as a patient and a magnetic resonance apparatus in side view at the beginning of an examination procedure, in which the local antenna device is still located in an initial position and the patient is still located outside of the magnetic resonance apparatus.

FIG. 1 shows a schematic side view of an embodiment of the examination platform 1 according to the invention, with a local antenna device 3 arranged above a patient bed 2 as well as a patient P and a magnetic resonance apparatus 13 in side view. The magnetic resonance apparatus 13 is coupled via an interface 23 with the examination platform 1 and has an acquisition space 14 that is surrounded by an annular or U-shaped (i.e. laterally open) tomography housing 15 in which are housed in a typical manner a whole-body radio-frequency coil, a basic field magnet, gradient coils, etc. For clarity, a further presentation of the technical details of a magnetic resonance apparatus 13 have not been included since these are known to those skilled in the art. The patient bed 2 can be moved along its longitudinal axis Z relative to a base 18 on rollers 10. The base 18 and the tomography housing 15 can also be fashioned as a combined housing. Other embodiments for a movable support of a patient bed 2 are known to those of ordinary skill in this field. Rail elements are another example. The drive for the patient bed 2 is not shown.

The local antenna 3 can be moved along a roll direction R relative to the patient bed 2 by means of the rollers 9. The movement is effected via a drive device 4, for example a rotation drive device, which is mechanically coupled with the local antenna device 3 via a shaft 8 and a shaft connection 16. Depending on the rotation direction of the shaft 8, the local antenna device 3 is moved in the direction of the drive device 4 or away from the drive device 4. The shaft 8 is furthermore mechanically supported via a shaft bushing 29.

Contained in the local antenna device 3 is an antenna 5 that serves for the acquisition of magnetic resonance signals. The antenna 5 can be formed as an individual antenna (as shown) or multiple antenna elements. An arrangement of multiple antenna elements in rows and columns in the form of an antenna array is possible. Typically antennas 5 are characterized by having an extent of less than 0.5 m (preferably essentially 0.4 m or less than 0.4 m) in the direction of the longitudinal axis Z of the patient bed 2.

Furthermore, a preamplifier 11 is schematically that which amplifies the magnetic resonance signals and relays them to a data acquisition unit of the magnetic resonance system for later image reconstruction. The relaying can ensue via wires or wirelessly (for example with electromagnetic waves or light signals). For hardwired relaying of the magnetic resonance signals, special embodiments such as electrically conductive guide rails or cable drag chains with flexible cables can be used in order to ensure reliable transfer of the magnetic resonance signals in spite of the movement capability of the local antenna device 3.

A control device 21 located in the bed device 1 controls the drive device 4 (and therefore the movement of the local antenna device 3) via a connection 2. Alternatively, such a control device 21 can be a component of a general controller of the magnetic resonance apparatus 13, or can even be independent of the bed device 1 or the magnetic resonance apparatus 13.

Figure 2:
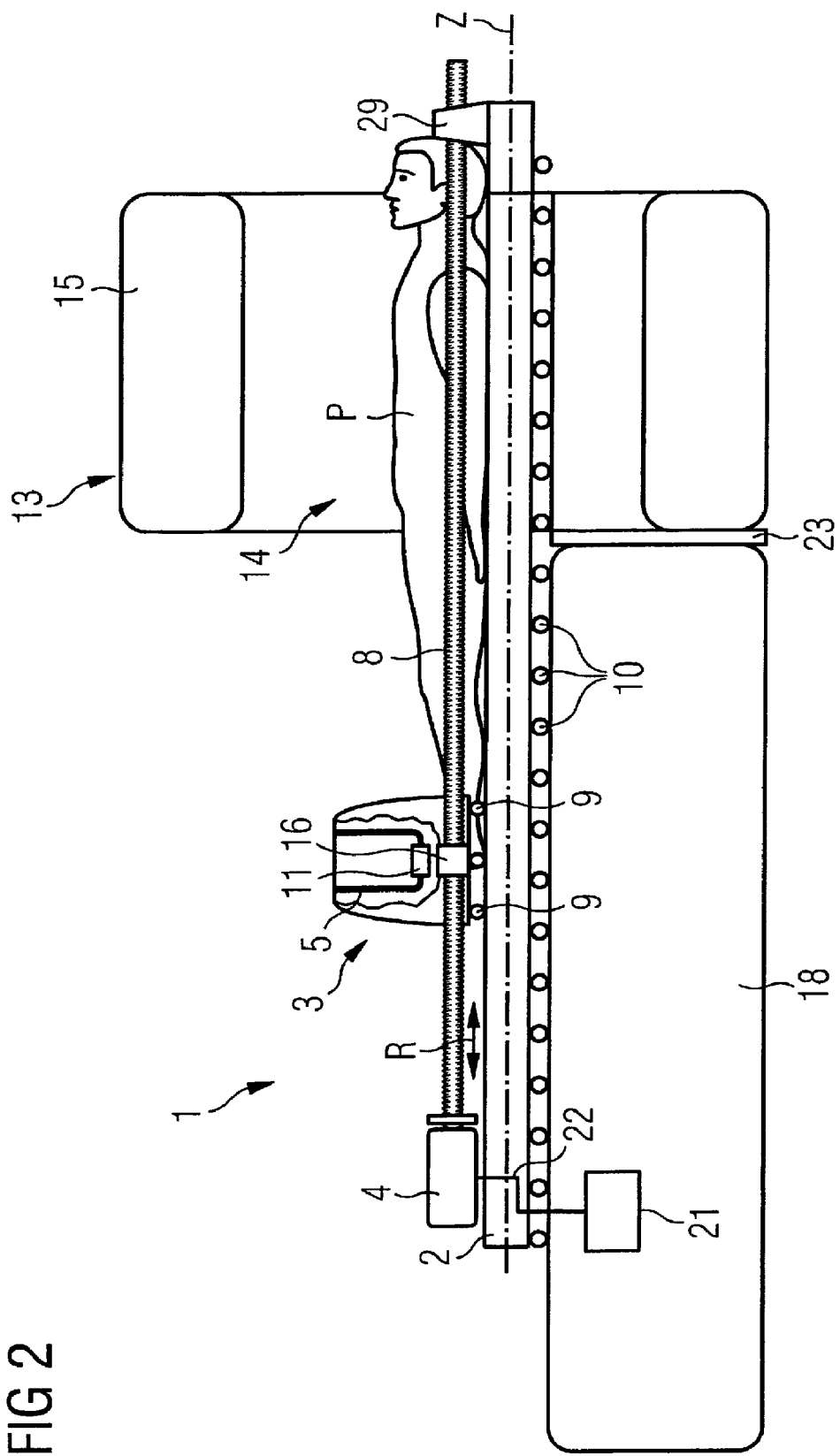
FIG. 2 is a side view corresponding to FIG. 1 after the patient has been inserted into the magnetic resonance apparatus.

FIG. 2 shows, as an example, a position of the local antenna device 3 and the patient bed 2 according to FIG. 1 after the patient P has been moved into the magnetic resonance apparatus 13 via a movement of the patient bed 2. Relative to FIG. 1, the local antenna device 3 has moved in the direction of the magnetic resonance apparatus 13 due to the movement of the patient bed 2. An additional movement of the local antenna device 3 has occurred in the direction of the head of the patient P due to the drive device 4, which can effect a movement of the local antenna device 3 independently of movement of the patient bed 2.

Figure 3:
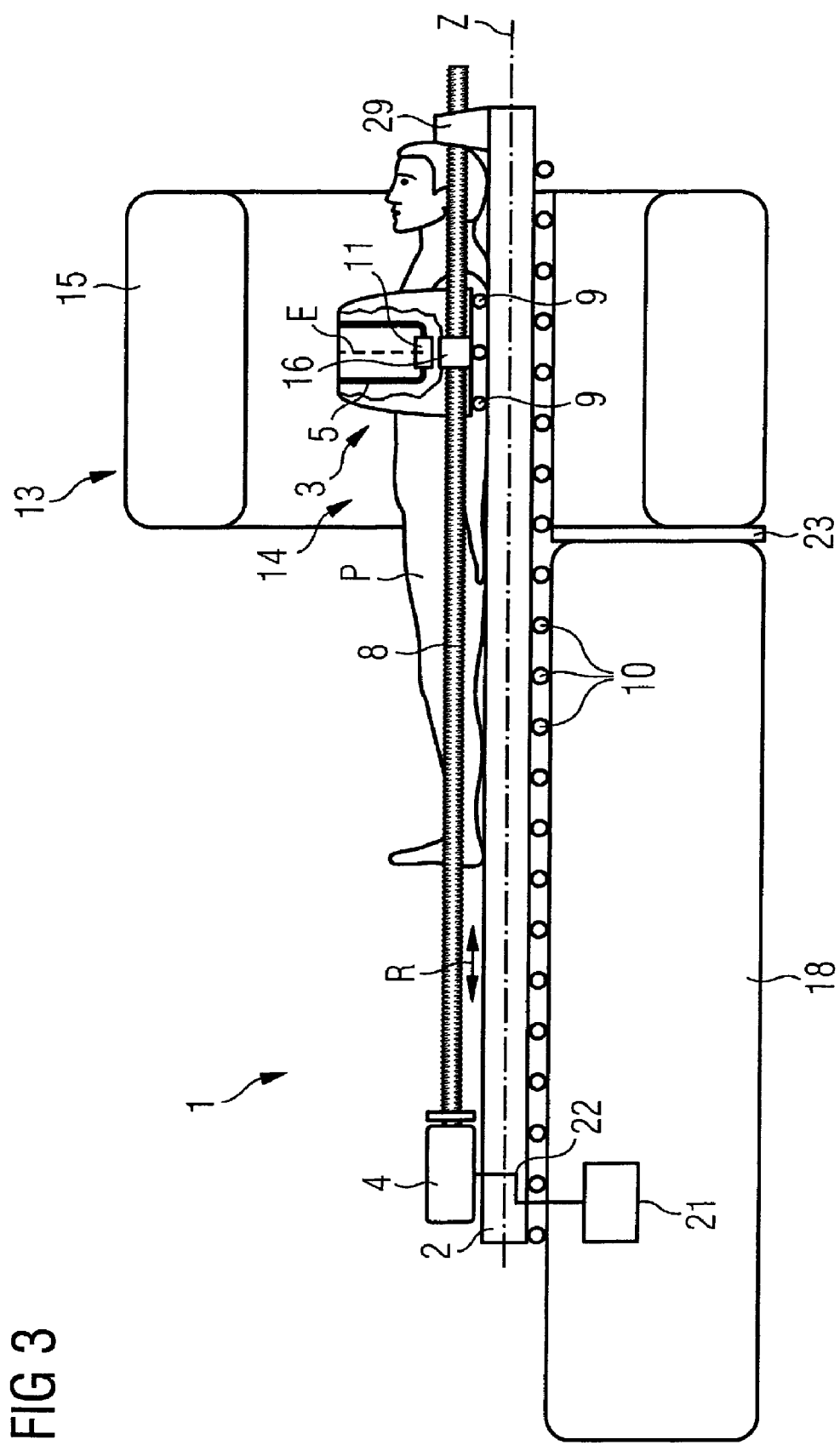
FIG. 3 is a side view corresponding to FIG. 1 at the beginning of an image acquisition procedure.

FIG. 3 shows an example of a position of the local antenna device 3 and the patient bed 2 according to FIGS. 1 and 2 at the beginning of an image acquisition process. Relative to FIG. 2, the local antenna device 3 has reached a position in the center of the magnetic resonance apparatus 13 by movement with the use of the drive device 4, and an image acquisition process can begin. If magnetic resonance data from various body regions of the patient P should be acquired, the patient P can be moved further along the longitudinal axis Z while the local antenna device 3 is kept in the center of the acquisition region 14 by a counter-movement with the use of the drive device 4.

Figure 4:
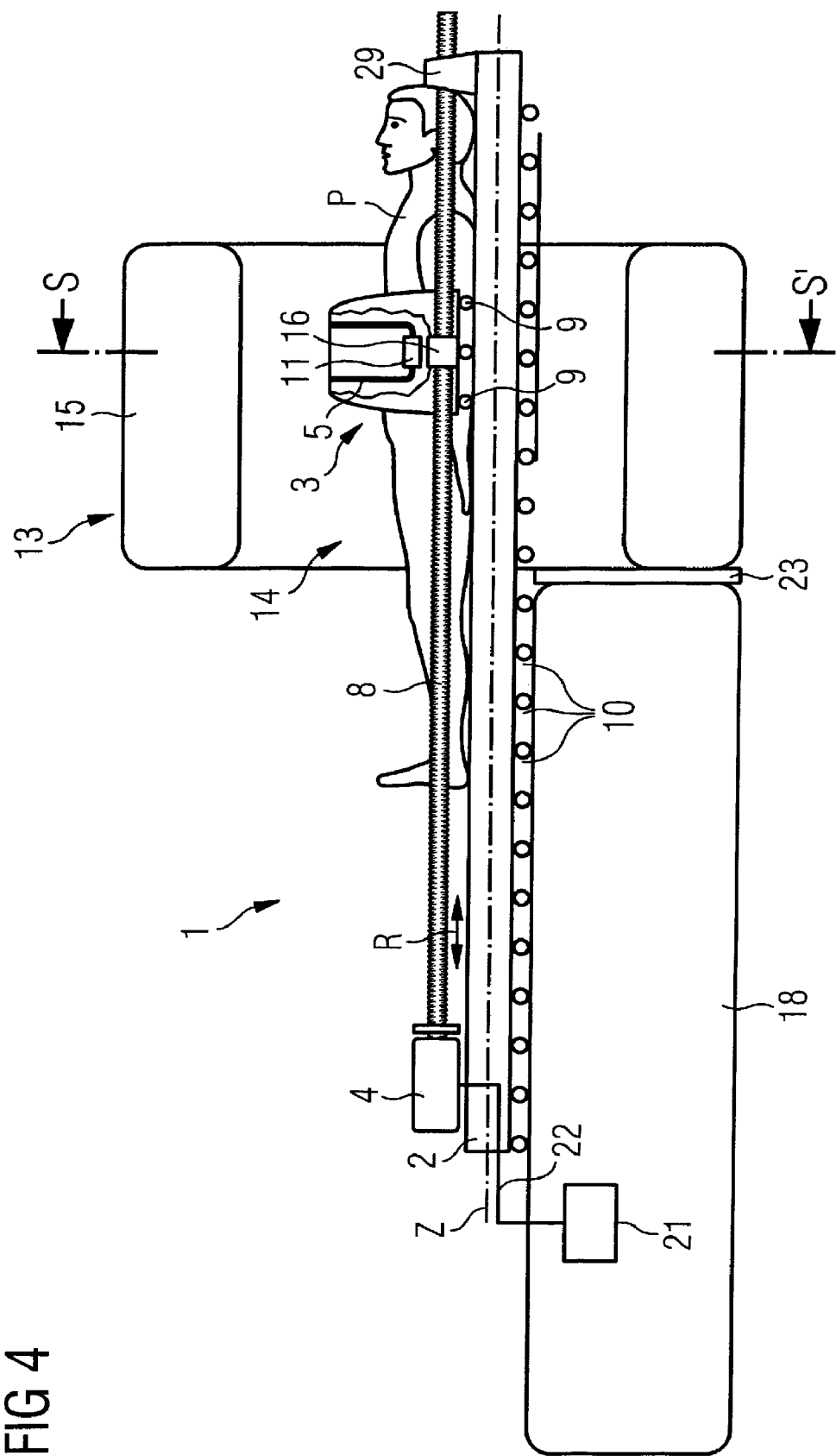
FIG. 4 is a side view corresponding to FIG. 1 at the end of an image acquisition procedure.

FIG. 4 shows an example a position of the local antenna device 3 and the patient bed 2 according to FIG. 1 through FIG. 3 at the end of an image acquisition process. Relative to FIG. 3, the patient P was moved further in the direction of his head. Moreover, a movement of the local antenna device 3 from the center of the acquisition region 14 has occurred independent of the movement of the patient P. Such a "decentering" is possible with the bed device 1 according to the invention and, for example, can serve to reduce couplings between the coils and antennas contained in the magnetic resonance apparatus 13.

Figure 5:
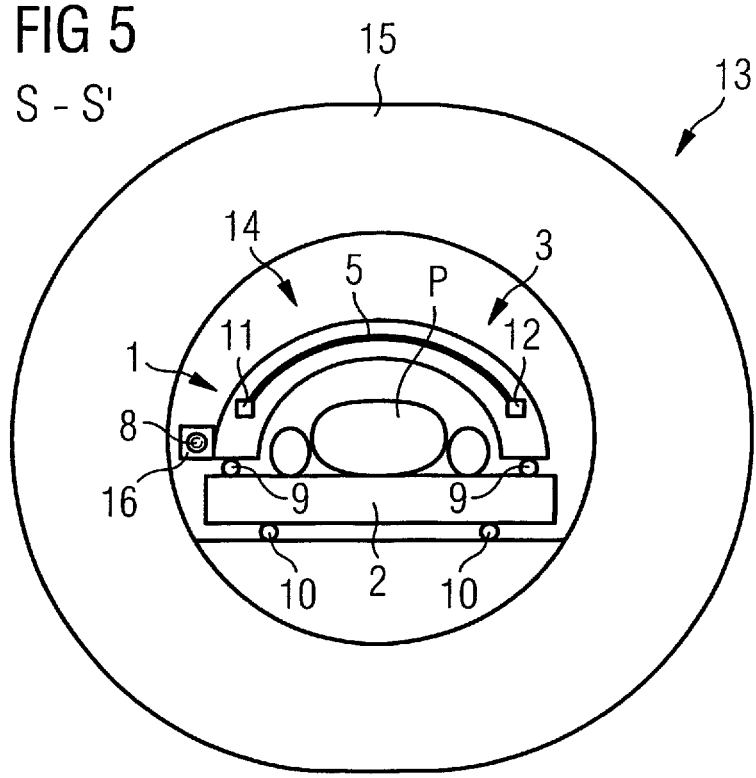
FIG. 5 is a schematic cross-section representation through the magnetic resonance apparatus according to FIG. 4 in the section plane S-S'.

FIG. 5 represents a schematic cross-section representation through the magnetic resonance apparatus 13 according to FIG. 4 along the slice plane S-S'. FIG. 5 in turn shows an examination platform 1 according to the invention with a local antenna device 3 arranged above a patient bed 2 as well as a patient P and a magnetic resonance apparatus 13. Relative to FIGS. 1 through 4, a detuning device 12 with which the acquisition properties of the antenna 5 can be adjusted is schematically shown. The local antenna device 3 exhibits a shape that largely follows a half circle arc. The patient P is spanned like a bridge by the local antenna device 3.

Figure 6:
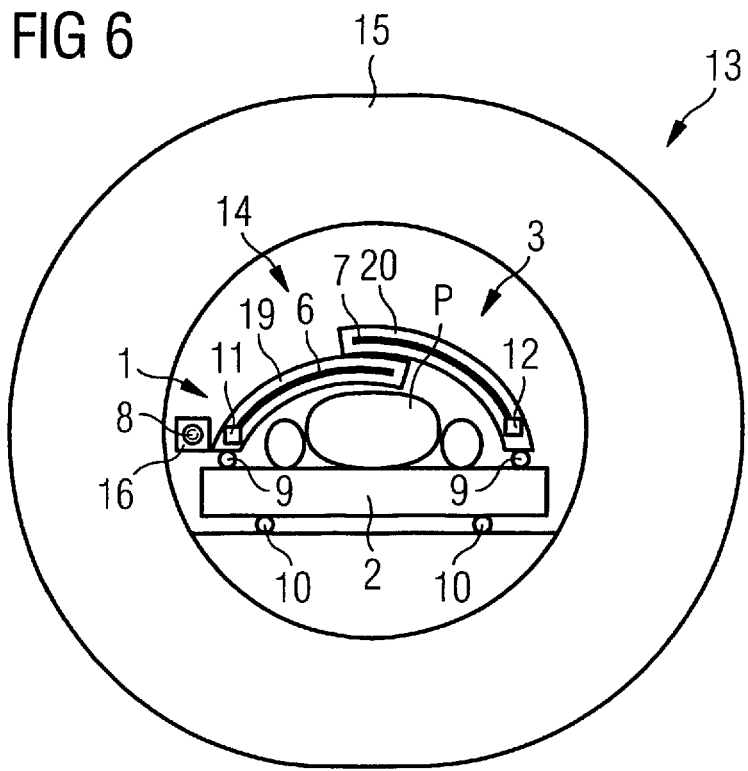
FIG. 6 is a schematic cross-section illustration through a magnetic resonance apparatus with an examination platform according to the invention, with two local antenna device elements arranged above a patient bed as well as a patient and a magnetic resonance apparatus.

FIG. 6 shows a further schematic cross-section representation through an alternative embodiment of the examination platform 3, wherein the examination platform 3 here includes two local antenna device elements 19, arranged over the patient P above a patient bed 2. The local antenna device elements 19, 20 are respectively partial antennas 6, 7. The complete antenna required for the image acquisition then arises through a galvanic and/or inductive and/or capacitive coupling between the partial antennas 6, 7. With such local antenna device elements 19, 20, the size of the encompassed space can be varied by a movement of the local antenna device elements 19, in a plane E perpendicular to the longitudinal axis Z of the patient bed 2. The distance between the partial antennas 6, 7 and the patient P thus can be individually adjusted in an advantageous manner so that a very slight distance from the patient P can be achieved. In principle, however, a mechanical design as is presented in FIG. 6 can also be realized in a form in which the overlapping elements contain coil elements or arrays independent of one another.

Figure 7:
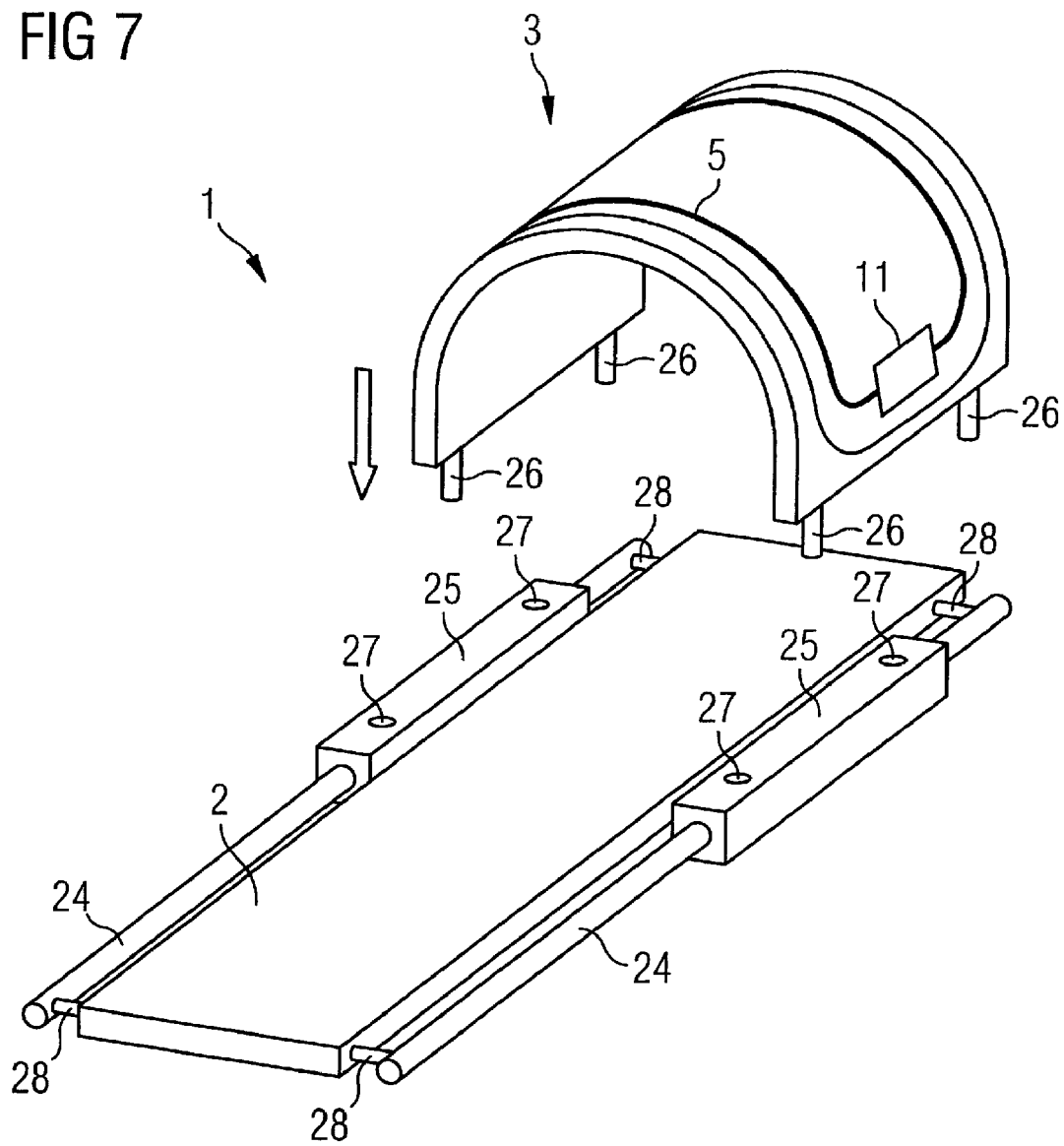
FIG. 7 is a schematic illustration of an examination platform according to the invention with local antenna device connected with the patient bed by rail elements.

FIG. 7 shows a schematic representation of a further exemplary embodiment of an examination platform according to the invention with a local antenna device 3 connected with the patient bed 2 via rail elements 24. The rail elements 24 are affixed with rail elements attachments 28 with regard to the patient bed 2. Bearing blocks 25 are mounted such that they can be displaced on the rail elements 24, and establish the connection between the local antenna device 3 and the rail elements 24. In an particularly advantageous embodiment of the invention, the local antenna device 3 is affixed with pegs 26 in bores 27 of the bearing blocks 25. In addition to a mechanical fixing, the pegs 26 can furthermore be used to relay magnetic resonance signals amplified by the preamplifier 11.

Figure 8:
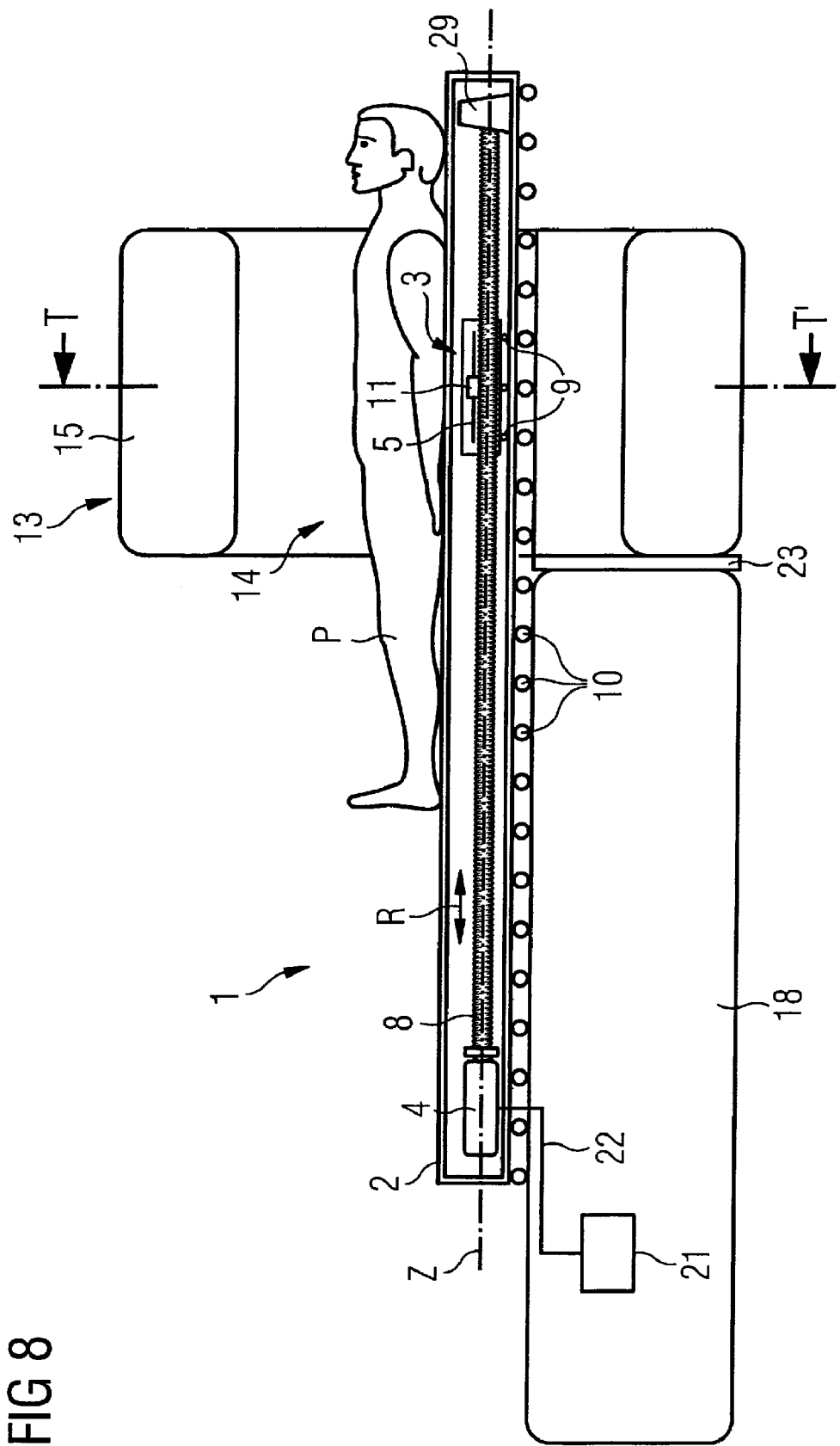
FIG. 8 is a schematic side view of an examination platform according to the invention, with a local antenna device integrated into a patient bed as well as a patient and a magnetic resonance apparatus in side view.

FIG. 8 shows a schematic representation of a side view of a further variant of an examination platform 1 according to the invention with a local antenna device 3 integrated into a patient bed 2. Corresponding to the embodiments of FIGS. 1 through 4, this particularly advantageous embodiment of the invention is also characterized in that the local antenna device 3 is movable independently of the patient bed 2. The local antenna device 3 integrated into the patient bed 2 is, for example, particularly suitable for examinations of the spinal column. Moreover, all components of the local antenna device 3 are integrated into the patient bed 2 so that local antennas 5 and their movement are not perceived as objectionable by the patient. Furthermore, in this embodiment the antenna 5 can be brought very close to the body of the patient so that image acquisitions of high quality can be achieved.

FIG. 9 is a schematic cross-section representation through the magnetic resonance apparatus 13 according to FIG. 8 along the slice plane T-T'. The local antenna device 3 is centrally arranged within the patient bed 2 and is moved by a shaft 8 centrally located in the local antenna device 3. Also shown is a detuning device 12. As can be seen from FIG. 9, the local antenna device 3 does not fill the void 17 shown in this cross-section representation. According to the invention it is therefore possible for the local antenna device 3 to additionally be moved perpendicular to the longitudinal axis Z of the patient bed 2. With such a movement the local antenna device 3 can be positioned under boundary regions of the patient P (for example under the arms) in order to also generate image acquisitions of these boundary regions.

The various examination platforms, magnetic resonance apparatuses and methods described in the preceding for acquisition of image data are exemplary embodiments that can be modified in many ways by those skilled in the field without departing from the scope of the invention.

In particular, the size ratios and shapes of the local antenna devices shown in FIGS. 1 through 9 can be presented differently than in the figures. Moreover, it is possible to form various combinations of the exemplary embodiments described above and to integrate local antenna devices that are arranged above the patient bed together with local antenna devices contained in the patient bed into a combined bed device. Both local antenna devices can be coupled via a common drive device or can be movable independently of one another by separate drive devices.

Although modifications and changes may be suggested by those skilled in the art, it is the intention of the inventors to embody within the patent warranted hereon all changes and modifications as reasonably and properly come within the scope of their contribution to the art.

We claim as our invention:

1. An examination platform for implementing a magnetic resonance examination, comprising:
    a patient bed configured to support a patient thereon to move the patient together with the patient bed along a longitudinal axis of the patient bed relative to a magnetic resonance data acquisition unit;
    a local antenna device configured to acquire magnetic resonance signals, said local antenna device being mounted on said patient bed for movement parallel to said longitudinal axis of the patient, independently of movement of the patient bed; and
    a drive device mounted at the patient bed and coupled to said local antenna device to move said local antenna device parallel to said longitudinal axis of the patient independently of movement of the patient bed.

2. An examination platform as claimed in claim 1 wherein said local antenna device is mounted above said patient bed and is configured to allow the patient on the patient bed to be at least partially positioned between the patient bed and the local antenna device.

3. An examination platform as claimed in claim 2 wherein said local antenna device has a bridge-like shape in a plane perpendicular to the longitudinal axis of the patient bed.

4. An examination platform as claimed in claim 2 wherein said local antenna device comprises at least a portion thereof formed of flexible materials, and comprising a bending device that interacts with said portion of said local antenna device to bend said portion to adjust a distance between the patient on the patient bed and said portion of said local antenna device.

5. An examination platform as claimed in claim 2 wherein said local antenna device comprises a first local antenna device element and a second local antenna device element, said first and second local antenna device elements being configured for respective movement in a plane perpendicular to the longitudinal axis of the patient bed.

6. An examination platform as claimed in claim 5 wherein each of said first and second local antenna device elements comprises at least one complete antenna.

7. An examination platform as claimed in claim 5 wherein said first local antenna device element comprises a first portion of an antenna and wherein said second local antenna device element comprises a second portion of said antenna, and wherein said first and second local device antenna elements are mounted on said patient bed for placement relative to each other to produce said antenna by a combination of said first portion and said second portion with a coupling therebetween selected from the group consisting of a capacitive coupling, and inductive coupling, and a galvanic coupling.

8. An examination platform as claimed in claim 1 wherein said local antenna device is at least partially integrated into said patient bed.

9. An examination platform as claimed in claim 1 wherein said local antenna device comprises at least one circuit component integrated therein, said at least one circuit component selected from the group consisting of preamplifiers and tuning devices.

10. An examination platform as claimed in claim 1 wherein said drive device is a drive selected from the group consisting of hydraulic drives, pneumatic drives and electromotive drives.

11. An examination platform as claimed in claim 1 comprising a plurality of rail elements mounting said local antenna device on said patient bed, said rail elements proceeding substantially parallel to said longitudinal axis of the patient bed.

12. An examination platform as claimed in claim 1 comprising a plurality of rollers mounting said local antenna device on said patient bed, said rollers being aligned in respective rows proceeding substantially parallel to the longitudinal axis of the patient bed.

13. A magnetic resonance apparatus comprising:
    a magnetic resonance data acquisition device having an opening therein; and
    an examination platform comprising a patient bed configured to support a patient thereon to move the patient together with the patient bed along a longitudinal axis of the patient bed relative to a magnetic resonance data acquisition unit, a local antenna device configured to acquire magnetic resonance signals, said local antenna device being mounted on said patient bed for movement parallel to said longitudinal axis of the patient, independently of movement of the patient bed, and a drive device mounted at the patient bed and coupled to said local antenna device to move said local antenna device parallel to said longitudinal axis of the patient independently of movement of the patient bed.

14. A magnetic resonance apparatus as claimed in claim 13 comprising a control device that controls operation of said drive device and movement of said patient bed to cause said local antenna device to always be located in a same position in an acquisition space in said opening of said data acquisition device during acquisition of image data with said data acquisition device, independently of a position of the patient bed in said opening.

15. A method for acquiring magnetic resonance data from a patient in a magnetic resonance apparatus, comprising the steps of:
    supporting a patient on a moveable patient bed that is movable along a longitudinal axis relative to a magnetic resonance data acquisition device;
    positioning the patient on the patient bed relative to an acquisition space in said opening by moving said patient bed with the patient thereon;
    mounting a local antenna device on said patient bed and providing said local antenna device with a drive device coupling thereto that moves said local antenna device independently of movement of the patient bed parallel to a longitudinal axis of the patient bed; and
    acquiring magnetic resonance signals from the patient with the local antenna device, representing magnetic resonance image data.

16. A method as claimed in claim 15 comprising controlling movement of said local antenna device and said patient bed to cause said local antenna device to always be located at a same position in said acquisition space during the acquisition of said magnetic resonance signals.

17. A method as claimed in claim 15 comprising moving said local antenna device in a plane perpendicular to said longitudinal axis of the patient bed at a time selected from the group consisting of before acquisition of said magnetic resonance signal and during acquisition of said magnetic resonance signals, to cause said local antenna device to converge in said plane relative to the patient.

18. A method as claimed in claim 15 comprising positioning the patient in the acquisition space exclusively by movement of the patient bed in a direction of the head of the patient, and moving the local antenna device in said direction of the head of the patient at a time selected from the group consisting of during movement of the patient bed and after movement of the patient bed.

* * * * *